(12) United States Patent
Wolf et al.

(10) Patent No.: US 7,754,655 B2
(45) Date of Patent: Jul. 13, 2010

(54) MICROCAPSULE FORMULATIONS

(75) Inventors: Hilmar Wolf, Langenfeld (DE); Peter Baur, Eppstein (DE); Manfred Zimmermann, Monheim (DE)

(73) Assignee: Bayer Cropscience AG, Monheim (DE)

( * ) Notice: Subject to any disclaimer, the term of this patent is extended or adjusted under 35 U.S.C. 154(b) by 798 days.

(21) Appl. No.: 10/515,590

(22) PCT Filed: May 16, 2003

(86) PCT No.: PCT/EP03/05163

§ 371 (c)(1), (2), (4) Date: May 9, 2005

(87) PCT Pub. No.: WO03/099005

PCT Pub. Date: Dec. 4, 2003

(65) Prior Publication Data

US 2005/0221991 A1 Oct. 6, 2005

(30) Foreign Application Priority Data

May 29, 2002 (DE) ................................ 102 23 916

(51) Int. Cl.
*A01N 25/28* (2006.01)
*B01J 13/02* (2006.01)
(52) U.S. Cl. .................. 504/359; 424/490; 424/408; 424/417; 264/4.1; 427/213.34; 514/963
(58) Field of Classification Search ............... 504/116, 504/359; 424/490, 408, 417; 514/963; 264/4.1; 427/213.34
See application file for complete search history.

(56) References Cited

U.S. PATENT DOCUMENTS

| | | | | |
|---|---|---|---|---|
| 3,577,515 A | 5/1971 | Vandegaer | .................. | 424/32 |
| 5,049,182 A * | 9/1991 | Scher et al. | .................. | 504/149 |
| 5,650,102 A | 7/1997 | Hagedorn et al. | | |
| 5,705,476 A | 1/1998 | Hoffarth | ..................... | 510/535 |
| 6,413,908 B1 | 7/2002 | Reekmans et al. | .......... | 504/116 |
| 6,602,823 B1 | 8/2003 | Röchling et al. | ......... | 504/116.1 |
| 2003/0087760 A1 | 5/2003 | Reekmans et al. | .......... | 504/118 |

FOREIGN PATENT DOCUMENTS

| | | |
|---|---|---|
| CA | 2385991 A1 * | 4/2001 |
| DE | 23 12 059 | 9/1973 |
| EP | 0 579 053 | 1/1994 |
| EP | 0548901 | 6/2000 |
| EP | 1 172 347 | 1/2002 |
| JP | 55104646 | 8/1980 |
| JP | 5238904 | 9/1993 |
| JP | 8224463 | 9/1996 |
| WO | 01/24631 | 4/2001 |

* cited by examiner

*Primary Examiner*—Johann R Richter
*Assistant Examiner*—Andriae M Holt
(74) *Attorney, Agent, or Firm*—Baker Donelson Bearman, Caldwell & Berkowitz, PC

(57) ABSTRACT

The invention relates to novel microcapsule formulations of
(A) a particulate disperse phase of microcapsules comprising
   (1) a polyurea and/or polyurethane coating with average layer thicknesses of between 5 and 20 nm, and
   (2) a capsule filling comprising at least one penetrant and, optionally, additives,
and
(B) a suspension comprising
   (1) at least one solid agrochemical active compound,
   (2) additives,
   (3) water, and
   (4) optionally, one or more agrochemical active compounds that are liquid at room temperature.

The invention further relates to a process for the preparation of these microcapsule formulations and to their use for applying agrochemical active compounds.

5 Claims, No Drawings

MICROCAPSULE FORMULATIONS

The present patent application has been filed under 35 U.S.C. 371 as a national stage application of PCT/EP03/05163, filed May 16, 2003, which was published in German as International Patent Publication WO 03/099005 on Dec. 4, 2003, and is entitled to the right of priority of German Patent Application 102 23 916.9, filed May 29, 2002.

The present invention relates to novel microcapsule formulations, to a process for their preparation, and to their use for the application of agrochemical active compounds.

It is already known to increase the biological activity of agrochemical active compounds by treating ready-to-use spray mixtures of agrochemical active compounds with penetrants or penetrant formulations and then applying these mixtures. However, the disadvantage of this process is that the components must he mixed immediately prior to application. This means that a uniform distribution of the penetrant in the preparation is not always ensured. Moreover, the accurate metering of the components is complicated.

Moreover, plant treatment compositions which, in addition to the agrochemical active compounds and customary additives, also comprise penetrants in the formulation have already been described. However, this type of preparation is frequently insufficiently stable for practical applications. Thus, one observes on many occasions that substantial active compound crystals form, which adversely affects the application of the spray mixtures, or indeed makes it impossible for them to be applied.

There have now been found novel microcapsule formulations composed of
A) a particulate disperse phase of microcapsules which have polyurea and/or polyurethane coatings with average layer thicknesses of between 5 and 20 nm and
   which comprise,
   as capsule filling,
      at least one penetrant and,
      if appropriate, additives,
   and
B) a suspension comprising
   at least one solid agrochemical active compound,
   additives,
   water and,
   if appropriate, one or more agrochemical active compounds which are liquid at room temperature.

It has furthermore been found that microcapsule formulations according to the invention can be prepared by
a) dispersing, in a first step, a mixture of
   at least one penetrant,
   at least one polyisocyanate from the group of the aliphatic isocyanates, aromatic isocyanates, cycloaliphatic isocyanates and/or the isocyanate of the formula

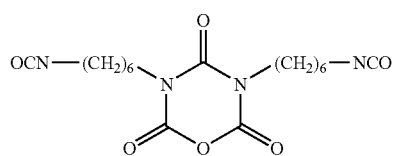

and,
   if appropriate, additives
   in an aqueous phase of
   one or more protective colloids,
   water and,
   if appropriate, one or more emulsifiers,
b) adding, in a second step, at least one diamine, polyamine, dialcohol, polyalcohol and/or aminoalcohol to the resulting mixture, and
c) if appropriate, freeing, in a third step, the resulting microcapsule dispersion from all or some of the liquid phase and then stirring it with a suspension of
   at least one solid agrochemical active compound,
   additives and,
   if appropriate, one or more agrochemical active compounds which are liquid at room temperature.

Moreover, it has been found that the microcapsule formulations according to the invention are highly suitable for applying the agrochemical active compounds present to plants and/or their environment.

Finally, it has been found that microcapsule preparations having p1 polyurea and/or polyurethane coatings with average layer thicknesses of between 5 and 20 nm and,
   as capsule filling,
      at least one penetrant and,
      if appropriate, additives,
   if appropriate as a mixture with
   one or more diluents and/or
   additives, are highly suitable for improving the efficacy of plant treatment compositions.

Surprisingly, the microcapsule formulations according to the invention display a markedly better and more rapid bioavailability of the agrochemical active compounds present than corresponding active compound suspensions in which no penetrants are present. Owing to the prior art, it was to be assumed that the penetrants can only be fully active when they are freely available in the formulations. As opposed to what was to be expected, however, even the microencapsulated penetrants are capable of increasing the bioavailability of agrochemical active compounds to the same extent.

The microcapsule formulations according to the invention are distinguished by a series of advantages. Thus, the product combinations of microencapsulated penetrant and active compound suspension can already be marketed by the producer in ready-to-use form. The laborious preparation of a tank mix immediately prior to application is not required. Another advantageous aspect is that the microcapsule formulations according to the invention are even stable when stored under practice conditions.

The microcapsule formulations according to the invention are characterized by the microcapsules present in the disperse phase and by the constituents which the suspension comprises.

The coatings of the microcapsules in the formulations according to the invention are polyureas and/or polyurethanes which are produced by reacting one or more polyisocyanates with diamines, polyamines, dialcohols, polyalcohols and/or aminoalcohols.

Suitable isocyanates are aliphatic, cycloaliphatic and aromatic di- or polyisocyanates, and the isocyanate of the formula

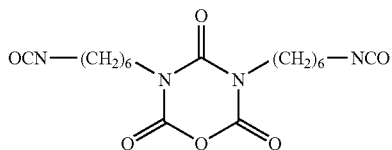

(I)

Examples which may be mentioned are
hexane 1,6-diisocyanate,
4,4'-methylene-bis-cyclohexyl isocyanate,
toluylene diisocyanate,
2H-1,3,5-oxadiazine-2,4,6-(3H,5H)-trione-3,5-bis-(6-isocyanato-hex-1-yl), of the formula (I)
diphenylmethane diisocyanate, and isomers and homologs thereof with higher functionality.

Amines which are suitable as reactants are, preferably, aliphatic and cycloaliphatic primary and secondary diamines and polyamines. Examples which may be mentioned are:

1,2-diaminoethane, diethylenetriamine, triethylenetetramine, bis-(3-aminopropyl)-amine, bis-(2-methylaminoethyl)methylamine, 1,4-diaminocyclohexane, 3-amino-1-methylaminopropane, N-methyl-bis-(3-aminopropyl)amine, 1,4-diamino-n-butane, 1,6-diamino-n-hexane and guanidine carbonate.

Also preferred are amines which are formed by reaction of the isocyanates mentioned above as being preferred with water.

Alcohols which are suitable as reactants are, preferably, primary or secondary aliphatic dialcohols or polyalcohols. Examples which may be mentioned are:

ethanediol, 1,2-propanediol, 1,3-propanediol, 1,4-butanediol, 1,5-pentanediol, 1,6-hexanediol, glycerol and diethylene glycol.

Furthermore preferred as reactants are aliphatic aminoalcohols such as, for example, triethanolamine.

Suitable penetrants which are present in the microcapsules of the formulations according to the invention are all customary substances which are capable of improving the penetration of agrochemical substances in plants. The following are preferably suitable: mineral oils, vegetable oils, esters of vegetable oils, fatty acid esters with 10 to 20 carbon atoms in the acid moiety and 1 to 10 carbon atoms in the alcohol moiety, esters of saturated or unsaturated dicarboxylic acids with 4 to 12 carbon atoms in the acid moiety and 1 to 8 carbon atoms in each alcohol moiety, esters of aromatic dicarboxylic acids with 1 to 8 carbon atoms in each alcohol moiety, and furthermore also alkanol alkoxylates.

Examples of penetrants which may be mentioned are:
mineral oils,
rapeseed oil, sunflower oil, corn oil, linseed oil, turnip rape oil, olive oil, cottonseed oil,
rapeseed oil methyl ester, rapeseed oil ethyl ester, turnip rape oil methyl ester, turnip rape oil ethyl ester,
ethylhexyl laurate,
dibutyl succinate, dibutyl adipate, dibutyl phthalate, and alkanol alkoxylates of the formula $$R—O—(AO)_m—R^1 \quad (I)$$

in which
R represents straight-chain or branched alkyl or alkylene with 4 to 20 carbon atoms,
AO represents an ethylene oxide radical, a propylene oxide radical, a butylene oxide radical or mixtures of ethylene oxide and propylene oxide radicals or butylene oxide radicals,
m represents numbers from 1 to 30 and
$R^1$ represents hydrogen or alkyl with 1 to 4 carbon atoms.

An especially preferred group of penetrants are alkanol alkoxylates of the formula $$R—O—(—EO—)_p—(—PO—)_q—R^1 \quad (Ia)$$

in which
R has the abovementioned meaning,
EO represents —$CH_2$—$CH_2$—O—,
PO represents

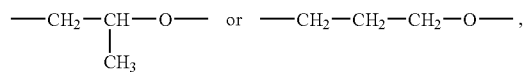

p represents numbers from 0 to 3,
q represents numbers from 1 to 6 and
$R^1$ represents hydrogen, methyl, ethyl, n-propyl, i-propyl or n-butyl, i-butyl.

A further especially preferred group of penetrants are alkanol alkoxylates of the formula $$R—O—(—PO—)_r—(EO—)_s—R^1 \quad (Ib)$$

in which
R has the abovementioned meaning,
EO represents —$CH_2$—$CH_2$—O—,
PO represents

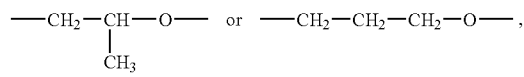

r represents numbers from 1 to 6,
s represents numbers from 1 to 3 and
$R^1$ represents methyl, ethyl, n-propyl, n-butyl or hydrogen.

A further especially preferred group of penetrants are alkanol alkoxylates of the formula

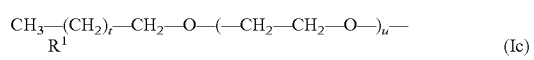

in which
t represents numbers from 8 to 13,
u represents numbers from 0 to 3 and
$R^1$ represents hydrogen, methyl, ethyl, n-propyl or n-butyl.

In the above formulae,
R preferably represents butyl, i-butyl, n-pentyl, i-pentyl, neopentyl, n-hexyl, i-hexyl, n-octyl, i-octyl, 2-ethyl-hexyl, nonyl, i-nonyl, decyl, n-dodecyl, i-dodecyl, lauryl, myristyl, i-tridecyl, trimethylnonyl, palmityl, stearyl or eicosyl.

As an example of an alkanol alkoxylate of the formula (Ib) 2-ethylhexyl alkoxylate of the formula

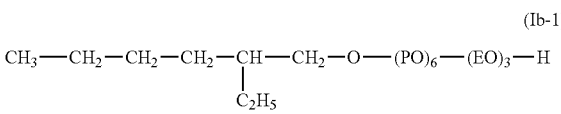

may be mentioned in which,

EO represents —CH$_2$—CH$_2$—O—,
PO represents

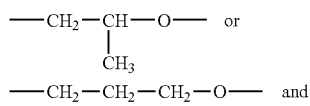

and the numbers 6 and 3 are averages.

Especially preferred alkanol alkoxylates of the formula (Ic) are compounds of this formula in which
t represents numbers from 9 to 12 and
u represents numbers from 0 to 3.

The alkanol alkoxylates are defined in general terms by the above formulae. These substances are mixtures of materials of the stated type with different chain lengths. This is why the indices calculated are averages, which may also be other than integers.

An example which may be mentioned is alkanol alkoxylate of the formula (Ic), in which
t represents the average value 10.5,
u represents the average value 3.0 and
R$^1$ represents methyl.

The alkanol alkoxylates of the formulae stated are known or can be prepared by known processes (cf. WO 98-35 553, WO 00-35 278 and EP-A 0 681 865).

Suitable additives which may be present in the microcapsules of the formulations according to the invention are emulsifiers and inert organic solvents.

Preferably suitable emulsifiers are anionic or neutral emulsifiers. An example which may be mentioned are styrylphenol alkoxylates.

Inert organic solvents which may be present are, preferably, aromatic hydrocarbons such as toluene, xylene or Solvesso®.

The suspension which is present in addition to the microcapsules in the formulations according to the invention comprises one or more agrochemical active compounds which are solid at room temperature. Agrochemical active compounds are understood as meaning, in the present context, fungicides, bactericides, insecticides, acaricides, nematicides, molluscicides, herbicides and plant growth regulators.

Examples of fungicides include:
2-anilino-4-methyl-6-cyclopropylpyrimidine; 2',6'-dibromo-2-methyl-4'-trifluoromethoxy-4'-trifluoromethyl-1,3-thiazol-5-carboxanilide; 2,6-dichloro-N-(4-trifluoromethylbenzyl)benzamide; (E)-2-methoximino-N-methyl-2-(2-phenoxyphenyl)-acetamide; 8-hydroxyquinoline sulfate; methyl (E)-2-{2-[6-(2-cyanophenoxy)-pyrimidin-4-yloxy]phenyl}-3-methoxyacrylate; methyl (E)-methoximino[alpha-(o-tolyloxy)-o-tolyl]acetate; 2-phenylphenol (OPP), ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chloroneb, chloropicrin, chlorothalonil, chlozolinate, cufraneb, cymoxanil, cyproconazole, cyprofuram, carpropamide, dichlorophen, diclobutrazole, dichlofluanid, diclomezin, dicloran, diethofencarb, difenoconazole, dimethirimol, dimethomorph, diniconazole, dinocap, diphenylamine, dipyrithione, ditalimfos, dithianone, dodine, drazoxolone, epoxyconazole, ethirimol, etridiazole, fenarimol, fenbuconazole, fenfuram, fenitropan, fenpiclonil, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, fenhexamide, guazatine, hexachlorobenzene, hexaconazole, hymexazole, imazalil, imibenconazole, iminoctadin, iprobenfos (ibp), iprodione, isoprothiolane, iprovalicarb, kasugamycin, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxine, probenazole, prochloraz, procymidon, propamocarb, propiconazole, propineb, pyrazophos, pyrifenox, pyrimethanil, pyroquilon, quintozene (PCNB), quinoxyfen, tebuconazole, tecloftalam, tecnazene, tetraconazole, thiabendazole, thicyofen, thiophanate-methyl, thiram, tolclophos-methyl, tolylfluanide, triadimefon, triadimenol, triazoxide, trichlamide, tricyclazole, triflumizole, triforine, triticonazole, trifloxystrobin, validamycin A, vinclozolin, zineb, ziram, 2-[2-(1-chlorocyclopropyl)-3-(2-chlorophenyl)-2-hydroxypropyl]-2,4-dihydro-[1,2,4]-triazole-3-thione 3-(1-[2-(4-[2-chlorophenoxy)-5-fluoropyrimid-6-yloxy)-phenyl]-1-(methoximino)-methyl)-5,6-dihydro-1, 4,2-dioxazine and N-methyl-2-(2-[6-(3-chloro-2-methylphenoxy)-5-fluoropyrmid-4-yloxy]phenyl)-2-methoximinoacetamide.

Examples of bactericides which may be mentioned are:
bronopol, dichlorophen, nitrapyrin, octhilinone, furancarboxylic acid, oxytetracyclin, probenazole, tecloftalam.

Examples of insecticides, acaricides and nematicides which may be mentioned are:
abamectin, acephate, acetamiprid, acrinathrin, alanycarb, aldicarb, alphamethrin, amitraz, avermectin, AZ 60541, azadirachtin, azinphos A, azinphos M, azocyclotin, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofluran, carbophenothione, carbosulfan, cartap, chloethocarb, chloretoxyfos, chlorfluazuron, chlormephos, N-[(6-chloro-3-pyridinyl)-methyl]-N'-cyano-N-methylethanimidamide, chlorpyrifos, chlorpyrifos M, cis-resmethrin, clocythrin, clofentezin, cyanophos, cycloprothrin, cyfluthrin, cyhalothrin, cyhexatin, cypermethrin, cyromazin, clothianidin, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, emamectin, esfenvalerate, ethiofencarb, ethofenprox, ethoprophos, fenamiphos, fenazaquin, fenbutatin oxide, fenobucarb, fenothiocarb, fenoxycarb, fenpropathrin, fenpyrad, fenpyroximate, fenvalerate, fipronil, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, oxamyl, oxydeprofos, permethrin, phosalon, phosmet, phosphamidon, pirimicarb, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, tebufenozide, tebufenpyrad, tebupirimiphos, teflubenzuron, tefluthrin, temephos, terbam, tetrachlorvinphos, thiacloprid, thiafenox, thiamethoxam, thiodicarb, thiofanox, thiomethon, thuringiensin, tralomethrin, transfluthrin, triarathen, triazuron, trichlorfon, triflumuron, trimethacarb, vamidothion, XMC, xylylcarb, zetamethrin.

Examples of molluscicides which may be mentioned are metaldehyde and methiocarb.

Examples of herbicides which may be mentioned are: anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxyphenoxyalkanoic esters such as, for example, diclofop-methyl, fenoxaprop-ethyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, metazachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb and tri-allate; triazines such as, for example, atrazine, cyanazine, simazine, simetryne, terbutryne and terbutylazine; triazinones such as, for example, hexazinon, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate, tridiphane, sulcotrione and propoxycarbazone-sodium. Others which may be mentioned are 4-amino-n-(1,1-dimethylethyl)-4,5-dihydro-3-(1-metylethyl)-5-oxo-1H-1,2,4-triazole-1-carboxamide and benzoic acid 2-((((4,5-dihdydro-4-methyl-5-oxo-3-propoxy-1H-1,2,4-triazol-1-yl)carbonyl)amino)sulfonyl) methyl ester.

Examples of plant growth regulators which may be mentioned are chlorcholine chloride and ethephon.

Suitable additives which may be present in the aqueous suspension of the formulations according to the invention are emulsifiers, dispersants, polyvinyl alcohol, protective colloids, antifoams, preservatives and thickeners. In this context, the suspensions comprise one or more of the additives.

Suitable emulsifiers and dispersants for the present purpose are, preferably, nonionic and anionic materials with surface-active properties.

Examples of nonionic emulsifiers which may be mentioned are the products known under the names Pluronic PE 10 100 (BASF) and Atlox 4913 (Uniqema). Others which are suitable are tristyrylphenol ethoxylates and N-alkylpyrrolidones. Examples of anionic emulsifiers which may be mentioned are lignosulfonates, naphthalenesulfonic acid/formaldehyde condensates, the product from Bayer AG known under the name Baykanol SL (=condensate of sulfonated ditolyl ether with formaldehyde) which is available commercially, and phosphated or sulfated tristyrylphenol ethoxylates, the specific mention being made of Soprophor SLK and Soprophor 4D 384 (Rhodia).

Protective colloids are all materials which can conventionally be employed for this purpose in plant treatment compositions. The following can preferably be used: polyvinyl alcohols, lignosulfonates, cellulose derivates, gum arabic, mixtures of polyvinyl alcohol and gum arabic, polyvinylpyrrolidones, polyacrylates, polymethacrylates and condensates of naphthalenesulfonic acids with formaldehyde.

Thickeners which are suitable are all substances which can conventionally be employed for this purpose in plant treatment compositions. Preferred are Kelzan® (xanthan-based thixotropic thickener), silicas and attapulgite.

Preservatives which are suitable are all substances which are usually present for this purpose in plant treatment compositions. Examples which may be mentioned are Preventol® (Bayer AG) and Proxel®.

Antifoams which are suitable are all substances which can conventionally be employed for this purpose in plant treatment compositions. Silane derivatives such as polydimethylsiloxanes and magnesium stearate may preferably be mentioned.

The aqueous suspension of the formulations according to the invention may additionally also comprise one or more agrochemical active compounds which are liquid at room temperature.

The composition of the microcapsule formulations according to the invention can be varied within a substantial range. In general, the disperse, encapsulated phase amounts to between 10 and 40% by weight, preferably between 15 and 35% by weight, based on the entire formulation.

The microcapsules consist of capsule coating and capsule content. The capsule coatings generally have a wall thickness of between 5 and 20 nanometers (=nm), preferably between 5 and 12 nanometers. The size of the microcapsules can be varied within a certain range. Thus, the mean diameter of the microcapsules is generally between 1 and 5 µm, preferably between 2 and 4 µm. The mean diameter is defined as 50% of the mass of all particles being smaller and 50% greater than this value.

The composition of the capsule content can likewise be varied within a certain range. The interior of the microcapsules generally comprise between 50 and 100% by weight, preferably between 70 and 100% by weight, of penetrant, and between 0 and 50% by weight, preferably between 0 and 30% by weight, of additives.

The amount of individual constituents in the aqueous phase of the microcapsule formulations according to the invention can be varied within a substantial range. Thus, the concentrations of solid agrochemical active compounds generally amount to between 5 and 40% by weight, preferably to between 10 and 35% by weight, of additives generally to between 2 and 15% by weight, preferably to between 3 and 12% by weight, of water to generally between 30 and 70% by weight, preferably to between 40 and 60% by weight, and of agrochemical active compounds which are liquid at room temperature generally to between 0 and 35% by weight, preferably to between 0 and 30% by weight.

The microcapsule formulations according to the invention are prepared in such a way that a microencapsulation is carried out first and the resulting microcapsule dispersion, if appropriate after partial or complete removal of the liquid phase, is mixed with a suspension of the desired composition Suitable components for carrying out the process according to the invention are preferably all those which have already been mentioned in connection with the description of the microcapsule formulations according to the invention as being preferred. In this context, the components are employed in such amount ratios that the concentrations of individual components in the resulting formulations are within the ranges which have already been mentioned.

The procedure in the first step of the process according to the invention is generally that a mixture of at least one penetrant, at least one polyisocyanate and, if appropriate, additives are dispersed with vigorous stirring in an aqueous phase of protective colloid, if appropriate in a mixture with one or more emulsifiers, and water. In this context, the ratio of penetrant to isocyanate can be varied within a certain range. In general, between 0.005 and 0.05 parts by weight, preferably between 0.005 and 0.04 parts by weight, of isocyanate are generally employed per part by weight of penetrant.

When preparing this mixture, the temperatures can be varied within a certain range. In general, the process is carried out at temperatures of between 10° C. and 100° C., preferably of between 20° C. and 90° C.

In the second step of the process according to the invention, the dispersion prepared in the first step is treated with at least one diamine, polyamine, dialcohol, polyalcohol and/or aminoalcohol, with gentle stirring, and stirring is then continued until the microencapsulation which takes place has ended.

In a particular variant of the process, di- or polyamine is generated by reacting, in the first step, isocyanate with water and then reacting the resulting di- or polyamine with the remaining polyisocyanate. In this case, a separate addition of amine is dispensed with.

When carrying out this second step of the process according to the invention, the ratio of isocyanate to amine component, or alkanol component, can be varied within a certain range. In general, 0.8 to 1.5 equivalents of amine component, or alkanol component, are employed per mole of isocyanate. The amounts of isocyanate and amine, or alkanol, are preferably chosen in such a way that equimolar amounts of isocyanate and amino groups, or hydroxyl groups, respectively, are present.

When carrying out the second step of the process according to the invention, the reaction temperatures can be varied within a certain range. In general, the process is carried out at temperatures between 40° C. and 80° C., preferably between 50° C. and 70° C.

In the third step of the process according to the invention, the previously formed microcapsule dispersion, either directly or after previous concentration, is stirred with a suspension of at least one solid agrochemical active compound, additives and, if appropriate, one or more liquid agrochemical active compounds which are liquid at room temperature. If the microcapsule dispersion is to be concentrated, such a procedure is preferably carried out at low temperatures and under reduced pressure.

The suspensions with which the microcapsule dispersions are stirred in the third step of the process according to the invention are suspension concentrates for agrochemical active compounds. In addition to active compound, these concentrates also comprise water and additives.

Suitable additives in this context are thickeners, preservatives, antifoams and dispersants. Substances which can preferably be used are those which have already been mentioned in connection with the description of the microcapsule suspensions according to the invention as being preferred thickeners, preservatives, antifoams and dispersants. Agrochemical. active compounds which are suitable in this context are those which have already been mentioned in connection with the description of the microcapsule dispersions according to the invention as being agrochemical components of the aqueous phase.

The amount ratios in which microcapsule dispersion and suspension concentrate can be mixed with one another can be varied within a substantial range. In general, the components are employed in such ratios that between 0.3 and 4 parts by weight, preferably between 0.5 and 3 parts by weight, of penetrant in microencapsulated form are present per part by weight of agrochemical active compound.

When carrying out the third step of the process according to the invention, the temperatures, again, can be varied within a certain range. In general, the process is carried out at temperatures of between 10° C. and 50° C., preferably of between 10° C. and 40° C.

In general, the process according to the invention is carried out under atmospheric pressure.

Microcapsule formulations according to the invention in which all components required for application are already present may be prepared in the above-stated manner. However, it is not necessarily required additionally to add concentrates of active compound suspensions to the microcapsule dispersions obtained after the second step. Instead, the microcapsule dispersion obtained after the second step may also be added to a commercially available suspension of one or more agrochemical active compounds at a later point in time, using the tank mix process.

The microcapsule formulations according to the invention are outstandingly suitable for applying the agrochemical active compounds which they comprise to plants and/or their environment. They ensure efficient penetration of the agrochemical active compounds which they comprise into the plants to be treated since the penetrants are fully active.

The microcapsule formulations according to the invention can be employed under practice conditions either as such or after previous dilution with water. In this context, application is affected by customary processes, i.e., for example, by pouring, spraying or atomizing.

The application rate of the microcapsule formulation according to the invention can be varied within a substantial range. It depends on the agrochemical active compounds in question and on their content in the microcapsule formulations.

The invention is illustrated by the examples which follow.

PREPARATION EXAMPLES

Example 1

A mixture of 215 g of ethylhexyl laurate and 4.8 g of toluylene diisocyanate is dispersed in the course of a minute at 23° C. in 227 g of a 1% by weight strength solution of polyvinyl alcohol (Mowiol 26-88®) in water as a mixture with 0.5 g of a silicone antifoam with the aid of a disperser at 10 000 rpm. Thereafter, 1.9 g of a 50% by weight strength solution of diethylenetriamine in water are added. The resulting reaction mixture is heated at 70° C. in the course of two hours and held at 70° C. for a further four hours, with gentle stirring. After the mixture has subsequently cooled to room temperature, 50 g of a 2% by weight strength solution of Kelzan S® (xanthan-based thickener) in water and 0.9 g of a preservative (Proxel GXL®) are added. This gives 500 g of a microcapsule formulation with an ethylhexyl laurate content of 43% by weight and a mean particle size of 3.9 μm.

Example 2

A mixture of 215 g of ethylhexyl laurate, 10.0 g Emulgator L3 (N-dodecylpyrrolidone) and 6.9 g of toluylene diisocyanate is dispersed in the course of a minute at 23° C. in 217.5 g of a 1% by weight strength solution of polyvinyl alcohol (Mowiol 26-88®) in water as a mixture with 0.5 g of a silicone antifoam with the aid of a disperser at 10 000 rpm. The resulting reaction mixture is heated at 70° C. in the course of two hours and held at 70° C. for a further four hours, with gentle stirring. After the mixture has subsequently cooled to room temperature, 50 g of a 2% by weight strength solution of Kelzan S® (xanthan-based thickener) in water are added. This gives 500 g of a microcapsule formulation with an ethylhexyl laurate content of 43% by weight and a mean particle size of 2.1 μm.

Example 3

A mixture of 1290 g of rapeseed oil, 6.45 g of Renex 36® (polyethylene oxide alkyl ether) and 22 g of toluylene-diisocyanate is dispersed in the course of a minute at 11° C. in 1442 g of a 1% by weight strength solution of polyvinyl alcohol (Mowiol 26-88®) in water as a mixture with 0.6 g of a silicone antifoam with the aid of a disperser at 10 000 rpm. Thereafter, 8.7 g of a 50% by weight strength solution of diethylenetriamine in water are added. The resulting reaction mixture is heated at 70° C. in the course of one hour and held at 70° C. for a further four hours, with gentle stirring. After the mixture has subsequently cooled to room temperature, 225 g of a 2% by weight strength solution of Kelzan S® (xanthan-based thickener) in water and 5.5 g of a preservative (Proxel GXL®) are added. This gives 3000 g of a microcapsule formulation with an rapeseed oil content of 32% by weight and a mean particle size of 3.2 μm.

Example 4

A mixture of 135 g of rapeseed oil methyl ester, 0.07 g of Emulgator L3 (N-dodecylpyrrolidone) and 2.5 g of toluylene diisocyanate is dispersed in the course of a minute at 15° C. in 138.8 g of a 1% by weight strength solution of polyvinyl alcohol (Mowiol 26-88®) in water as a mixture with 0.06 g of a silicone antifoam with the aid of a disperser at 10 000 rpm. Thereafter, 0.49 g of a 50% by weight strength solution of diethylenetriamine in water are added. The resulting reaction mixture is heated at 70° C. in the course of one hour and held at 70° C. for a further four hours, with gentle stirring. After the mixture has subsequently cooled to room temperature, 15 g of a 2% by weight strength solution of Kelzan S® (xanthan-based thickener) in water and in each case 0.3 g of Preventol D2® and Preventol D7® (preservative) are added. This gives 300 g of a microcapsule formulation with a rapeseed oil methyl ester content of 45% by weight and a mean particle size of 2.9 μm.

Example 5

A mixture of 120 g of rapeseed oil ethyl ester, 3.71 g of a solution of 44.7% by weight of toluylene diisocyanate, 35.3% by weight of Desmodur® 44 V 20 L and 20% by weight of Solvesso 200® is dispersed in the course of a minute at 15° C. in 153.1 g of a 1% by weight strength solution of polyvinyl alcohol (Mowiol 26-88®) in water as a mixture with 0.06 g of a silicone antifoam with the aid of a disperser at 8000 rpm. The resulting reaction mixture is heated at 70° C. in the course of one hour and held at 70° C. for a further four hours, with gentle stirring. After the mixture has subsequently cooled to room temperature, 7.5 g of water and 15 g of a 2% by weight strength solution of Kelzan S® (xanthan-based thickener) in water and in each case 0.3 g of Preventol D2® and Preventol D7® (preservative) are added. This gives 300 g of a microcapsule formulation with a rapeseed oil ethyl ester content of 40% by weight and a mean particle size of 2.5 μm.

Example 6

A mixture of 120 g of rapeseed oil ethyl ester, 2.1 g of toluylene diisocyanate and 1.6 g of 4,4'-methylene-bis-(cyclohexyl)isocyanate is dispersed in the course of a minute at 17° C. in 153.1 g of a 1% by weight strength solution of polyvinyl alcohol (Mowiol 26-88®) in water as a mixture with 0.06 g of a silicone antifoam with the aid of a disperser at 8000 rpm. The resulting reaction mixture is heated at 70° C. in the course of one hour and held at 70° C. for a further four hours, with gentle stirring. After the mixture has subsequently cooled to room temperature, 22.5 g of a 2% by weight strength solution of Kelzan S® (xanthan-based thickener) in water and in each case 0.3 g of Preventol D2® and Preventol D7® (preservative) are added. This gives 300 g of a microcapsule formulation with an rapeseed oil ethyl ester content of 40% by weight and a mean particle size of 2.5 μm.

Example 7

A solution of 120 g of rapeseed oil ethyl ester, 2.50 g of Desmodur T 80® (Bayer AG) and 1.21 g of hexamethylene 1,6-diisocyanate is dispersed in the course of a minute at 23° C. in 153.1 g of a 0.9% by weight strength solution of polyvinyl alcohol (Mowiol 26-88®) in water as a mixture with 0.06 g of a silicone antifoam with the aid of a disperser at 8000 rpm (rotations per minute). The mixture is heated at 70° C. in the course of one hour and held at 70° C. for a further four hours, with gentle stirring. After the mixture has subsequently cooled to room temperature, 22.5 g of a 2% by weight strength solution of Kelzan S® (xanthan-based thickener) in water and 0.6 g of preservative (0.3 g of Preventol D2® and 0.3 g of Preventol D7®) are added. This gives 300 g of a microcapsule formulation with a mean particle size of 2.51 μm and an average theoretical wall thickness of 12 nm.

Example 8

451 g of tebuconazole are mixed with 30 g of an ethylene oxide/propylene oxide block polymer, 1 g of a silicone antifoam and 296 g of water. The mixture is first comminuted coarsely and then ground to the desired degree of fineness with the aid of a bead mill. After addition of 50 g of glycerol, 2 g of preservative (Preventol D7®) and 50 g of a 2.0% by weight strength aqueous solution Kelzan S®, 1000 g of a suspension concentrate with a tebuconazole content of 500 g/l are obtained.

Example 9

40 g of the suspension concentrate of Example 8 and 40 g of the microcapsule formulation of Example 7 and 10 g of propanediol, 4 g of a 2.0% by weight aqueous solution of Kelzan S®, 0.2 g of preservative (Preventol D7®) and 5.8 g of water are mixed with gentle stirring. This gives 100 g of a formulation comprising 18% by weight of tebuconazole and 16% by weight of rapeseed oil ethyl ester.

Use Example/Penetration Test

This test measured the penetration of active substance through enzymatically isolated cuticles of apple tree leaves.

The leaves used were cut in fully developed state from apple trees of the Golden Delicious variety. The cuticles were isolated as follows:

first of all, leaf discs labeled on the underside with dye and formed by punching were filled by means of vacuum infiltration with a pectinase solution (0.2 to 2% strength) buffered to a pH of between 3 and 4, then sodium azide was added and the leaf discs thus treated were left to stand until the original leaf structure broke down and the non-cellular cuticles underwent detachment.

Subsequently, only those cuticles from the top leaf sides which were free from stomata and hairs were used. They were washed a number of times in alternation with water and with a buffer solution with a pH of 7. The clean cuticles obtained were, finally, applied to Teflon platelets, smoothed with a gentle airjet and dried.

In the next step, the cuticle membranes obtained in this way were placed in diffusion cells (i.e. transport chambers) made of stainless steel for membrane transport investigations. For these investigations the cuticles were placed centrally using tweezers on the edges of the diffusion cells, which were coated with silicone grease, and were sealed with a ring, which was likewise greased. The arrangement had been chosen so that the morphological outer face of the cuticles was pointing outwards, i.e. to the air, while the original inner face was facing the inside of the diffusion cell. The diffusion cells were filled with water or a mixture of water and solvent.

To determine the penetration, 9 µl of a spray liquor of the composition indicated below were applied to the outer face of each cuticle.

Spray Mixture A 10 g of the formulation of Example 9 are diluted with such an amount of demineralized water that a spray mixture with a tebuconazole content of 0.6 g/l results.

Spray Mixture B 10 g of a commercially available tebuconazole suspension concentrate are treated with such an amount of demineralized water that a spray mixture with a tebuconazole content of 0.6 g/l results.

After the spray mixtures have been applied, the water was evaporated in each case, then each of the chambers was inverted and placed in thermostated troughs, containing in each case a saturated aqueous calcium nitrate tetrahydrate solution below the outer face of the cuticles. The penetration which occurred took place at a relative atmospheric humidity of 56% and a set temperature of 25° C. At regular intervals, samples were taken with a syringe and analyzed by HPLC for the amount of penetrated active compound.

The test results can be seen from the table which follows. The figures shown are averages of 8 measurements.

TABLE

| Spray mixture | Active compound penetration after 2 days | Standard deviation |
| --- | --- | --- |
| A (according to the invention) | 10.92% | ±2.65% |
| B (known) | 0.23% | ±0.46% |

What is claimed is:

1. A agrochemical formulation comprising
   (A) a particulate disperse phase of microcapsules having
      (1) a polyurea and/or polyurethane coating having an average layer thickness of between 5 and 20 nm, and
      (2) a capsule filling comprising at least one penetrant and, optionally, additives,
   and
   (B) a suspension present on the exterior surface of said coating comprising
      (1) at least one solid agrochemical active compound,
      (2) additives,
      (3) water, and
      (4) optionally, one or more agrochemical active compounds that are liquid at room temperature.

2. A process for the preparation of agrochemical formulations according to claim 1 comprising
   (a) in a first step, dispersing a mixture of
      (1) at least one penetrant,
      (2) at least one polyisocyanate selected from the group consisting of aliphatic isocyanates, aromatic isocyanates, cycloaliphatic isocyanates, and the isocyanate of the formula

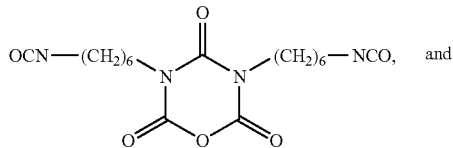

(3) optionally, additives
      in an aqueous phase comprising
      (1) one or more protective colloids,
      (2) water, and
      (3) optionally, one or more emulsifiers,
   (b) in a second step, adding to the mixture formed in step (a) at least one diamine, polyamine, dialcohol, polyalcohol, and/or aminoalcohol, and
   (c) in a third step, after optionally freeing the microcapsule dispersion obtained in step (b) from all or a portion of the liquid phase, stirring the microcapsule dispersion with a suspension comprising
      (1) at least one solid agrochemical active compound,
      (2) additives, and
      (3) optionally, one or more agrochemical active compounds that are liquid at room temperature.

3. A method of applying an agrochemical active compound to plants comprising applying a agrochemical formulation according to claim 1 to plants and/or their environment.

4. A microcapsule preparation comprising microcapsules having
   (1) a polyurea and/or polyurethane coating having an average layer thickness of between 5 and 20 nm, and (2) a capsule filling comprising at least one penetrant and, optionally, additives, optionally as a mixture with one or more diluents and/or additives, and optionally,
(3) a suspension present on the exterior surface of said coating comprising
   (a) at least one solid agrochemical active compound,
   (b) additives, and
   (c) water,
   (d) where optionally, one or more of said agrochemical active compounds are liquid at room temperature.

5. A method of improving the efficacy of plant treatment compositions comprising incorporating the plant treatment composition into a microcapsule preparation according to claim 4.

* * * * *